US00PP12304P2

(12) United States Plant Patent
Shibamichi

(10) Patent No.: US PP12,304 P2
(45) Date of Patent: Dec. 25, 2001

(54) CAMELLIA PLANT NAMED 'ELINA CASCADE'

(75) Inventor: Akira Shibamichi, Kawasguchi (JP)

(73) Assignee: Hines Nurseries, Inc., Irvine, CA (US)

( * ) Notice: Subject to any disclaimer, the term of this patent is extended or adjusted under 35 U.S.C. 154(b) by 0 days.

(21) Appl. No.: 09/411,664

(22) Filed: Oct. 4, 1999

(51) Int. Cl.[7] ..... A01H 5/00

(52) U.S. Cl. ..... Plt./243

(58) Field of Search ..... Plt./243, 244

*Primary Examiner*—Bruce R. Campell
*Assistant Examiner*—June Hwu
(74) *Attorney, Agent, or Firm*—Christie, Parker & Hale, LLP

(57) ABSTRACT

A new plant variety of *Camellia tsaii* var. *synaptica* characterized by its production of attractive pink buds and flowers with petals having a pink base, and its pendulous, weeping growth habit.

5 Drawing Sheets

BACKGROUND OF THE INVENTION

The present invention relates to a new and distinct variety of *Camellia tsaii* var. *synaptica*, which was discovered in 1991 as a seedling selection in a controlled planting of *Camellia tsaii* var. *synaptica* (unpatented) in Kawasguchi City, Japan. The varietal denomination of the new variety is 'ELINA CASCADE'.

The genus Camellia is included in the family Theaceae which comprises about 25 genera shrubs and trees, mostly tropical and subtropical in origin, and native to the northern and southern hemispheres. Camellia comprises more than 80 species of evergreen shrubs or trees, many of which possess desirable ornamental characteristics.

*Camellia tsaii* var. *synaptica* (Sealy) Chang (1981) is an evergreen upright growing shrub widespread and common throughout Yunnan and Hunan Provinces, China, Burma and North Vietnam. Flowers are pure white with 5 petals. The backs of flower bracts are glabrous. Leaves are thick, glossy and dark green in color. Young shoots are thicker than the species.

SUMMARY OF THE INVENTION

The new variety was discovered in 1991 as a seedling in a controlled planting of *Camellia tsaii* var. *synaptica* in Kawasguchi City, Japan, by Mr. Akira Shibamichi. 'ELINA CASCADE' differs from its parent and all other varieties of *Camellia tsaii* var. *synaptica* known to the inventor in having pink flower buds and flowers with petals having pink bases, and a pendulous, weeping growth habit. Asexual reproduction of the new variety by stem cuttings performed in Saitama Prefecture, Japan; Lewisberry, Pa.; Vacaville, Calif.; Irvine, Calif.; and Flushear, Tex.; have confirmed that the distinctive characteristics of the new variety are stable and transmitted to succeeding generations, and the new variety reproduces true to type.

COMPARISON WITH PARENT

The new variety was discovered in 1991 as a seedling in a controlled planting of *Camellia tsaii* var. *synaptica* in Kawasguchi City, Japan. 'ELINA CASCADE' differs from its parent and all other varieties of *Camellia tsaii* var. *synaptica* known to the inventor in having pink flower buds and flowers with petals having pink bases, and a pendulous, weeping growth habit. Asexual reproduction of the new variety by stem cuttings performed in Saitama Prefecture, Japan; Lewisberry, Pa.; Vacaville, Calif.; Irvine, Calif.; and Fulshear, Tex.; have confirmed that the distinctive characteristics of the new variety are stable and transmitted to succeeding generations, and the new variety reproduces true to type.

DESCRIPTION OF ILLUSTRATIONS

The accompanying illustrations show a plant of the new variety in a photographic illustrations as true to color as is reasonably possible to make in illustrations of this character.

DETAILED DESCRIPTION OF THE NEW VARIETY

Figure 1:
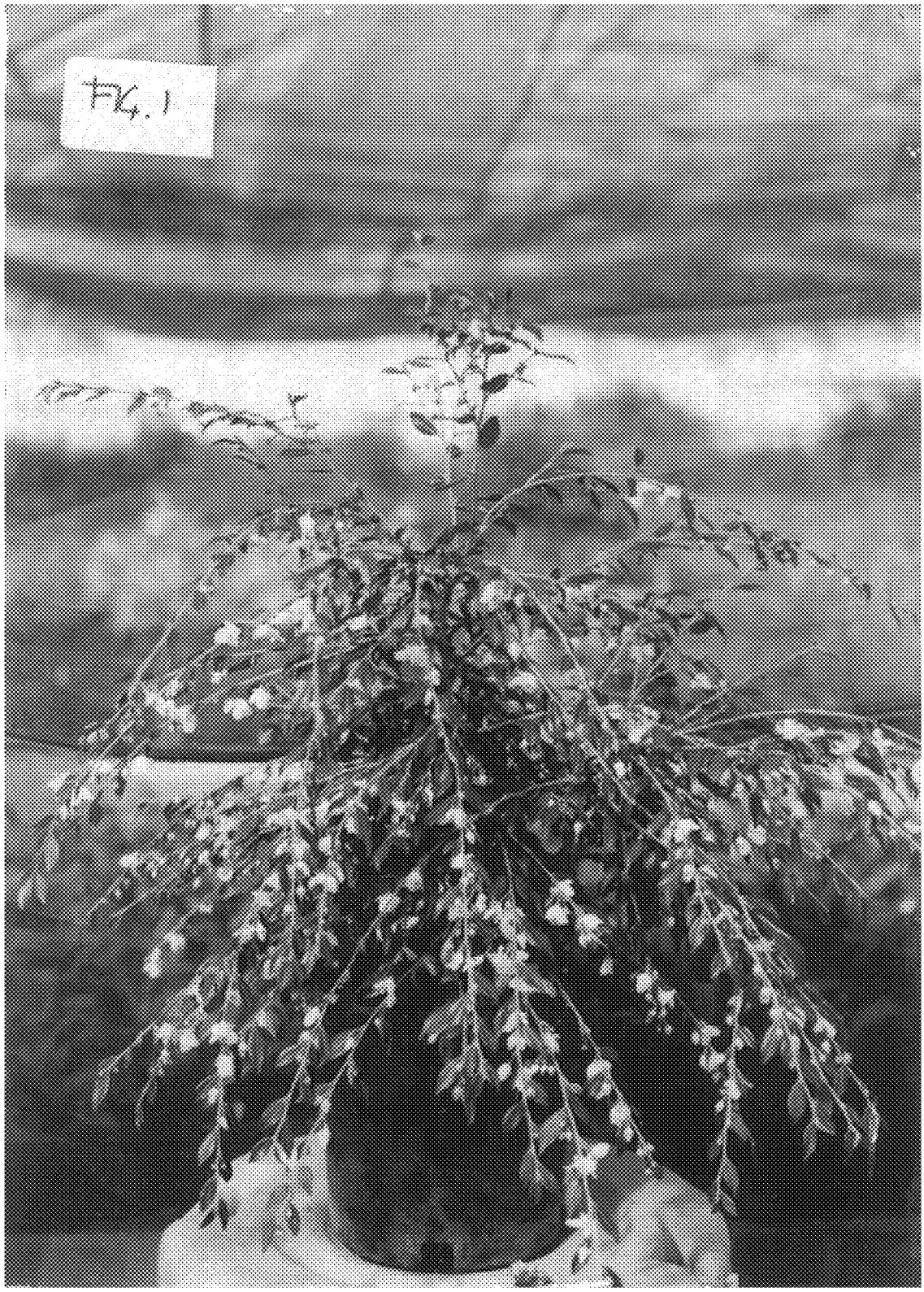
FIG. 1 illustrates the variety in bloom and its characteristic pink infloresence; the pendulous growth habit of the variety is also illustrated.
Figure 2:
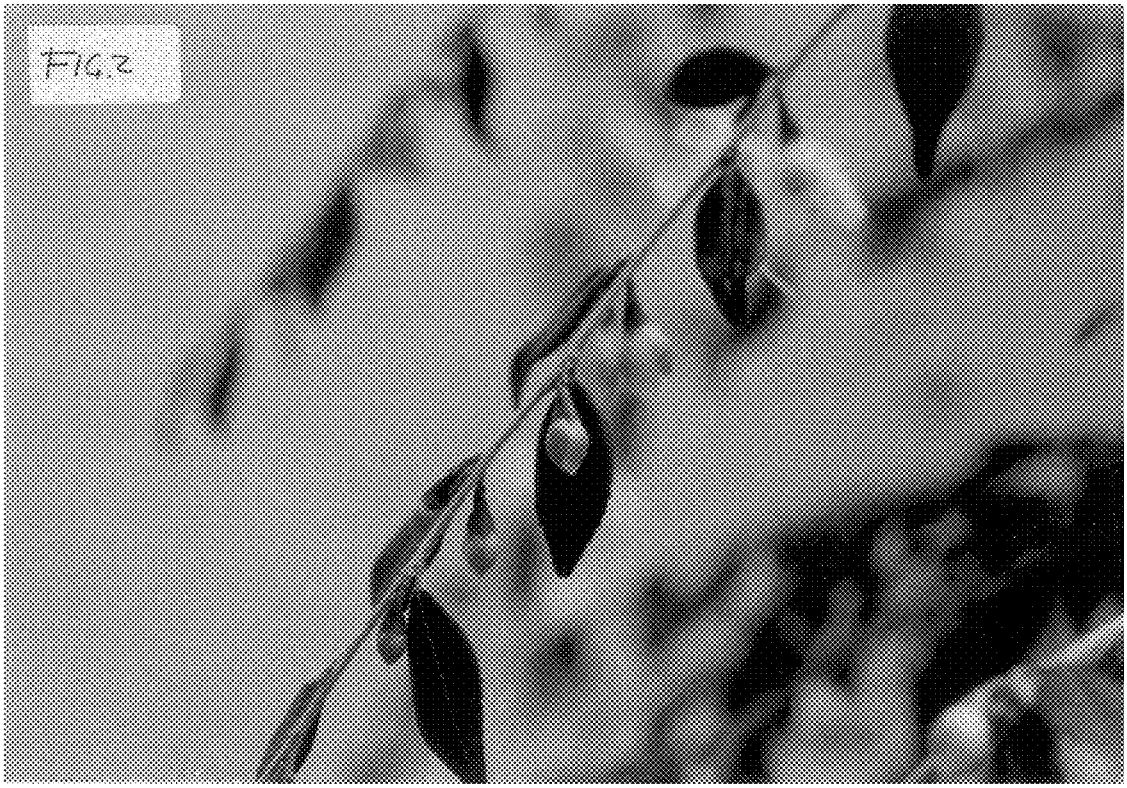
FIG. 2 illustrates closed flower bud of the new variety; note the characteristic pink coloration of the closed bud.
Figure 3:
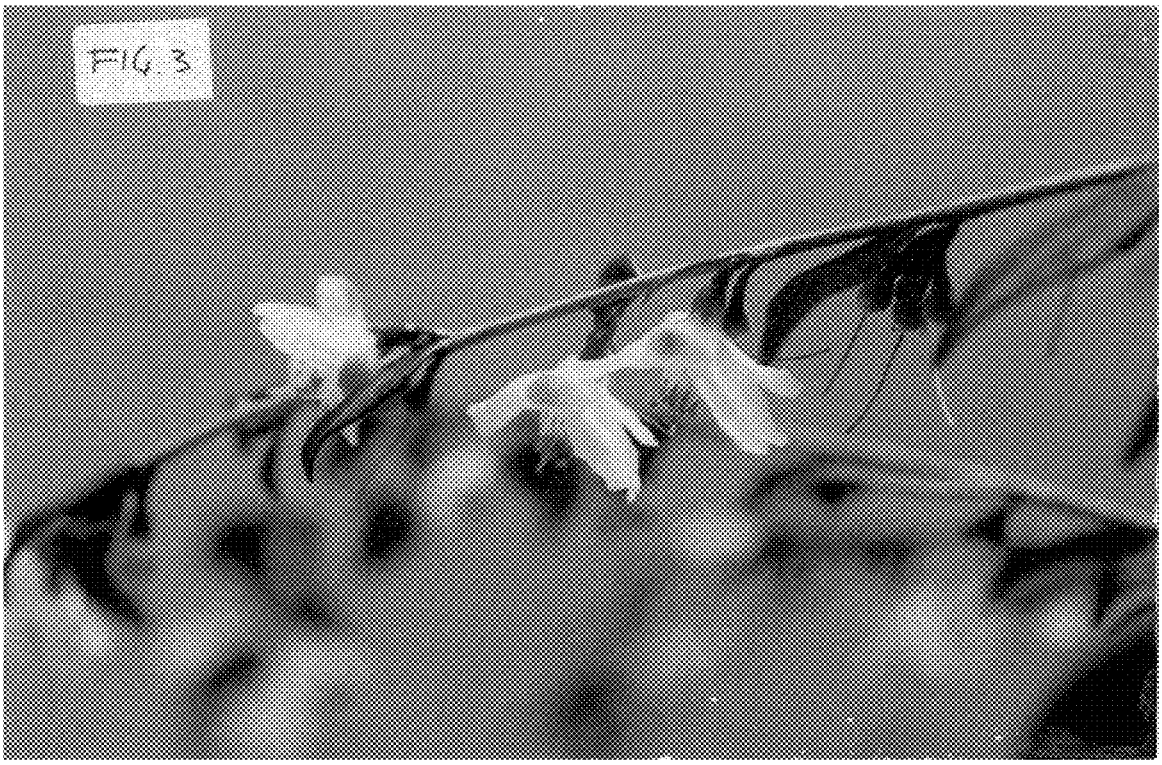
FIG. 3 illustrates the flower of the new variety when in bloom; note the characteristic pink coloration of the petals.
Figure 4:
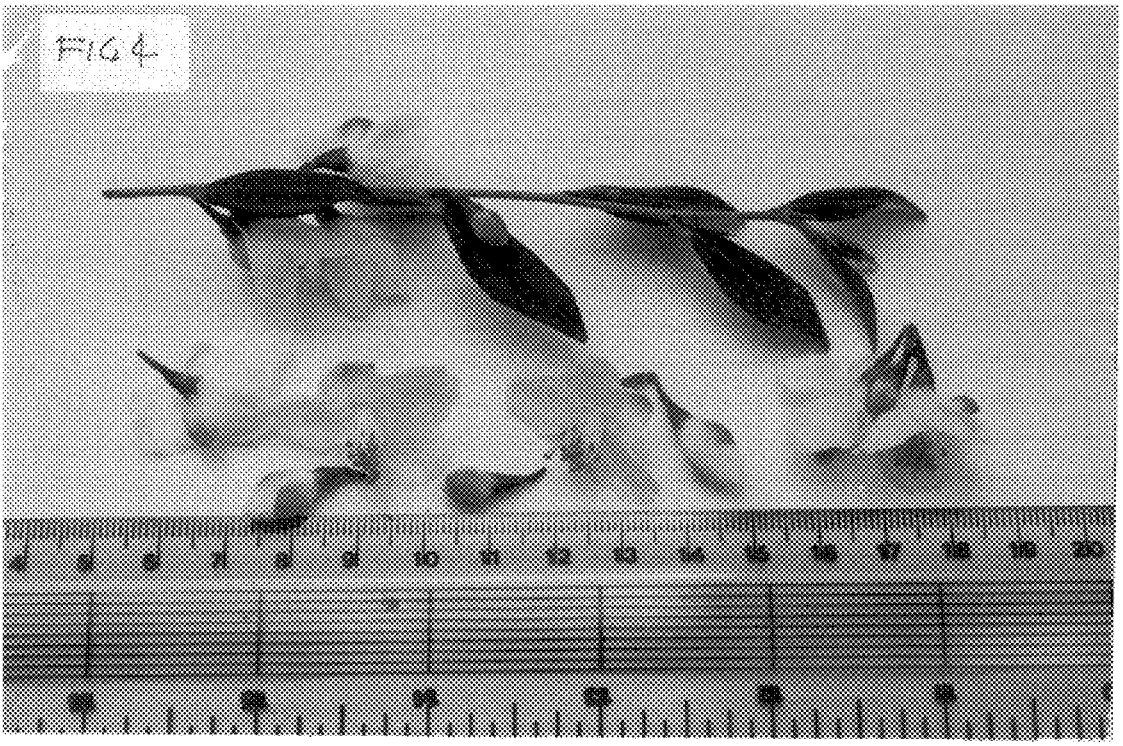
FIG. 4 illustrates the approximate scale of the flower bud, open flower, as well as the foliage.
Figure 5:
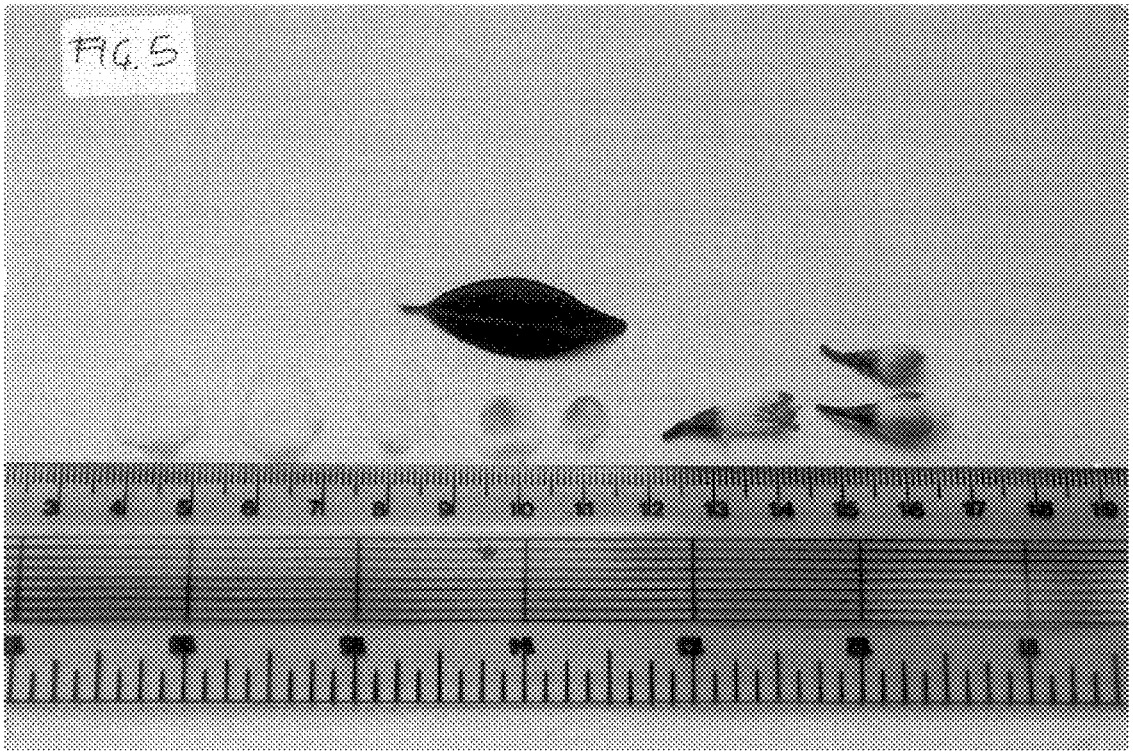
FIG. 5 illustrates the flower parts, including the outer petals and inner petals; note the characteristic pink coloration of the outer petals and the slight pink coloration of the primarily white inner petals.

'ELINA CASCADE' has not been observed under all possible environmental, cultural and light conditions. The following observations and descriptions are of plants grown in containers at Lewisberry, Pa., and Vacaville, Calif. The following observations and descriptions are of 3-year-old plants, in 5-gallon nursery containers, grown in an unheated greenhouse with 70% shade during summer months, in a production nursery setting in Vacaville, Calif. In this description, color references are to *The Royal Horticultural Society Colour Chart* (1995) and terminology used in the color descriptions herein refers to plate numbers in this color chart. Phenotypic expression may vary with light intensity, cultural and environmental conditions.

Classification:

*Botanical.*—*Camellia tsaii* var. *synaptica* (Sealy) Chang (1981) 'ELINA CASCADE'.

*Parentage.*—Chance seedling in a controlled planting of *Camellia tsaii* var. *synaptica* (unpatented).

*Propagation.*—By stem cuttings.

Plant:

*Size.*—Mature plant can grow to height of about 2 m tall and about 2 m wide.

*Habit.*—Evergreen shrub with a pendulous, weeping growth habit.

*Branching.*—Overall habit of plant is weeping; from central leader, most lateral branches are ascending or slightly ascending for one-quarter to one-half of their length, then oblique to strongly descending to a 45° angle; strong terminal growth and lateral branching near base of plant is less weeping.

Leaf:

*Shape.*—Elliptical.

*Apex.*—Acuminate.

*Base.*—Cuneate.

*Size.*—From about 2.5 to 4.5 cm long and from about 1 to 2 cm wide.

*Arrangement.*—Alternate.

*Margin.*—Serrulate; slightly turned down at the edges.

*Texture/substance.*—Upper side: Coriaceous. Under side: Coriaceous.

*Color.*—Upper side: Near Green Group 139A. Under side: Near Green Group 138A.

*Venation.*—Reticulate.

*Petioles.*—Size: From about 3.0 to 3.5 mm long. Color: Near Group 199C (new growth). Texture/Substance: New growth is hirsute.

*Hardiness.*—USDA Zone 8 (10° F. to 20° F.).

*Vigor.*—Approximately 18" over 12-month period on young plants, slowing as plant matures.

*Pests/diseases.*—None noted.

Inflorescence:

*Bloom period.*—Mid to late winter (in unheated greenhouse).

*Flower form.*—Campanulate at anthesis, petals spreading the flower ages, becoming salviform.

*Flower arrangement.*—Pedicellate, pendulous, flowers are usually borne solitary, occasionally in twos or threes, at each node, hanging either straight down or at an angle within 45° of straight down.

*Flower size.*—From about 1.6 to 2.0 in diameter.

*Fragrance.*—None.

*Lastingness of individual blooms.*—From about 10 to 14 days.

*Petals.*—5.

*Color.*—Outer Petals: About 1 to 3 (typically 2) of the outer petals of each flower have a white background stained with reddish-pink, near Red Group 53C; the stain is variable in size and intensity depending on light and temperature, but typically covers the center and tip of the outside of each petal that is pigmented; the bases of the stained petals are normally white, near White Group 155C. Inner Petals: About 1 to 3 of the outer petals of each flower have a white background stained with reddish-pink, near Red Group 53C; the stain is variable in size and intensity depending on light and temperature, but typically covers the center and tip of the outside of each petal that is pigmented; the bases of the stained petals are normally white, near White Group 155C; when the plant is in tight bud, the buds appear to be reddish pink nearly all over, except at the base of the bud. In Bud: When the plant is in tight bud, the buds appear to be reddish pink nearly all over, except at the base of the bud. Open Flower: As the flower opens, the entirely white inner petals are revealed and the reddish-pink stain is seen only on some of the outside petals; the landscape effect from a distance is that the shrub in flower is perceived to be light pink overall, but at close range it is clear that the flowers are not pink but white irregularly stained with reddish-pink.

Reproductive organs:

*Androecium.*—Stamens Number: From about 23 to 28. Size: From about 5 to 10 mm long; less than 1 mm in diameter. Color: White, near White Group 155A. Pollen color: Near Yellow-Orange Group 21B.

*Gynoecium.*—Pistil Size: Approximately 12 mm long, barely split into 3 segments. Color: Near White Group 155A. Fruit Type: Elliptical; about 3 or 4 segments. Length: Approximately 1 cm. Diameter: Approximately 14 mm. Color: Near Greyed-Orange Group 166B. Seed: None observed.

I claim:

1. A new plant variety of *Camellia tsaii* var. *synaptica* of the variety substantially as shown and described.

* * * * *